United States Patent
Röttger et al.

(10) Patent No.: US 7,026,523 B2
(45) Date of Patent: Apr. 11, 2006

(54) METHOD FOR TELOMERIZING NON-CYCLIC OLEFINS

(75) Inventors: Dirk Röttger, Recklinghausen (DE); Matthias Beller, Rostock (DE); Ralf Jackstell, Wittenberg (DE); Holger Klein, Rostock (DE); Klaus-Diether Wiese, Haltern (DE)

(73) Assignee: OXENO Olefinchemie GmbH, Marl (DE)

( * ) Notice: Subject to any disclaimer, the term of this patent is extended or adjusted under 35 U.S.C. 154(b) by 107 days.

(21) Appl. No.: 10/478,697

(22) PCT Filed: May 4, 2002

(86) PCT No.: PCT/EP02/04909

§ 371 (c)(1),
(2), (4) Date: Dec. 9, 2003

(87) PCT Pub. No.: WO02/100803

PCT Pub. Date: Dec. 19, 2002

(65) Prior Publication Data

US 2005/0038273 A1    Feb. 17, 2005

(30) Foreign Application Priority Data

Jun. 9, 2001   (DE) .................. 101 28 144

(51) Int. Cl.
C07C 43/15    (2006.01)

(52) U.S. Cl. .............. 585/638; 585/639; 556/136; 560/244; 560/265; 564/485; 568/690

(58) Field of Classification Search .......... 556/136; 585/638, 639; 568/690; 560/244, 265; 564/485

See application file for complete search history.

(56) References Cited

U.S. PATENT DOCUMENTS

| | | | |
|---|---|---|---|
| 4,831,183 A | 5/1989 | Hanes | |
| 5,834,611 A | 11/1998 | Driessen-Helscher et al. | |
| 6,548,684 B1* | 4/2003 | Indolese et al. | 556/14 |
| 6,613,910 B1* | 9/2003 | Grubbs et al. | 548/103 |
| 6,627,782 B1 | 9/2003 | Kaizik et al. | |
| 2004/0059170 A1 | 3/2004 | Rottger et al. | |
| 2004/0242947 A1 | 12/2004 | Beller et al. | |

FOREIGN PATENT DOCUMENTS

| | | |
|---|---|---|
| DE | 2 151 662 | 5/1972 |
| WO | 91/09822 | 7/1991 |

OTHER PUBLICATIONS

U.S. Appl. No. 10/497,034, filed May 28, 2004, Beller et al.
Jackstell, Ralf et al. "A Highly Efficient Catalyst for the Telomerization of 1,3-Dienes with Alcohols: First Synthesis of a Monocarbenepalladium(0)-Olefin Complex", Angew, Chem. Int. Ed., vol. 41, No. 6, pp. 986-989, XP001111654 2002.
U.S. Appl. No. 10/538,475, filed Jun. 07, 2005, Kaizik et al.
U.S. Appl. No. 10/538,359, filed Jun. 13, 2005, Rottger et al.
U.S. Appl. No. 10/517,620, filed Dec. 23, 2004, Rottger et al.
U.S. Appl. No. 10/490,038, filed Mar. 19, 2004, Beller et al.
U.S. Appl. No. 10/478,697, filed Dec. 09, 2003, Rottger et al.
U.S. Appl. No. 10/470,280, filed Aug. 08, 2003, Rottger et al.
U.S. Appl. No. 6,627,782, filed Sep. 30, 2003, Kaizik et al.

* cited by examiner

*Primary Examiner*—Fred Teskin
(74) *Attorney, Agent, or Firm*—Oblon, Spivak, McClelland, Maier & Neustadt, P.C.

(57) ABSTRACT

The invention provides a process for the telomerization of acyclic olefins having at least two conjugated double bonds (I) or mixtures comprising such olefins by means of nucleophiles (II) using a palladium-carbene complex as catalyst.

15 Claims, No Drawings

METHOD FOR TELOMERIZING NON-CYCLIC OLEFINS

The present invention relates to a process for the telomerization of acyclic olefins having at least two conjugated double bonds (I) by means of nucleophiles (II) using a palladium complex as catalyst.

For the purposes of the present invention, telomerization is the reaction of olefins having conjugated double bonds (conjugated dienes) in the presence of a nucleophile (telogen). Main products obtained are compounds made up of two equivalents of the diene and one equivalent of the nucleophile.

The products of the telomerization reaction have industrial importance as versatile precursors for solvents, plasticizers, fine chemicals and intermediates for active compounds. The compounds octadienol, octadienyl ether and octadienyl esters obtainable from butadiene are potential intermediates in processes for preparing corresponding alkenes.

The telomerization of dienes by means of nucleophiles is an industrially interesting method of upgrading inexpensive, industrially available dienes. Owing to their ready availability, the use of butadiene, isoprene or cracker fractions comprising these dienes is of particular interest. However, up to the present time, the telomerization of butadiene has been employed in practice only by the company Kuraray in the fine chemicals field for the synthesis of 1-octanol. Reasons why telomerization processes have not been used more widely include unsatisfactory catalyst activities, catalyst productivities and selectivity problems associated with telomerization catalysts. Thus, the known telomerization processes lead to high catalyst costs and/or by-products which prevent industrial implementation.

Halogen-free palladium(0) and palladium(II) compounds have been found to be effective catalysts for telomerization (A. Behr, in "*Aspects of Homogeneous Catalysis*", editor: R. Ugo, D. Reidel Publishing Company, Doordrecht/Boston/Lancaster, 1984, Vol. 5, 3). In addition, compounds of other transition metals, e.g. cobalt (R. Baker, A. Onions, R. J. Popplestone, T. N. Smith, *J. Chem. Soc., Perkin Trans. II* 1975, 1133–1138), rhodium, nickel (R. Baker, D. E. Halliday, T. N. Smith, *J. Organomet. Chem.* 1972, 35, C61–C63; R. Baker, *Chem. Rev.* 1973, 73, 487–530; R. Baker, A. H. Cook, T. N. Smith, *J. Chem. Soc., Perkin Trans. II* 1974, 1517–1524) and platinum have also been used as catalysts. However, the latter systems are inferior to palladium complexes in respect of activity and selectivity.

Telomerization has been comprehensively described in the technical literature. The abovementioned known catalysts generally give, for example in the telomerization of butadiene by means of methanol, mixtures of the products 1a, 1b, 2, 3 shown, where X=O, $R^1$=Me. Main products are the desired industrially important linear telomers 1a and 1b. However, significant proportions of the branched telomer 2 and of 1,3,7-octatriene 3 are formed.

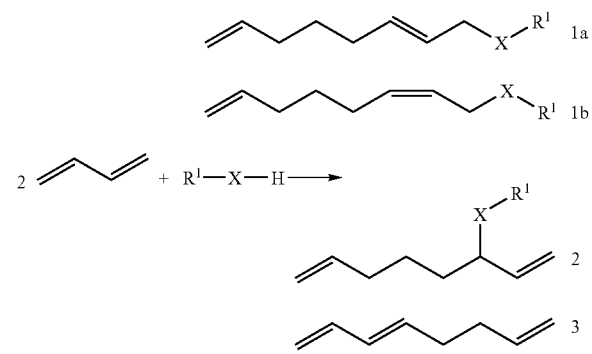

Variable yields of 4-vinyl-1-cyclohexene (Diels-Alder product of butadiene) are also formed, as are, generally in only small amounts, further by-products. This product spectrum is generally also found when using other nucleophiles having active H atoms, with the methoxy group being replaced by the corresponding radicals of the respective nucleophile.

Significant formation of the by-products mentioned is a further reason for implementation of an economical and environmentally friendly process being extraordinarily difficult. Thus, the abovementioned problems cannot be solved satisfactorily despite the fact that the telomerization of butadiene by means of methanol has been intensively researched and patented by a number of companies.

In a continuous process which has been described by Dow Chemical in WO 91/09822 in 1989 and uses palladium acetylacetonate/2 equivalents of triphenylphosphine as catalyst, catalyst productivities (turnover numbers) up to 44 000 were achieved. However, the chemoselectivities to the target product 1 at such catalyst turnover numbers are <85%.

In 1987, National Distillers and Chem. Corp. (U.S. Pat. Nos. 4,642,392, 4,831,183) described a batch process for preparing octadienyl ethers. In this process, the product mixture was separated by distillation from the catalyst (palladium acetate/5 equivalents of triphenylphosphine) which remained as a solution in tetraglyme. The catalyst can then be reused up to twelve times, with supplementary phosphine being added each time. However, the starting batch gave the linear ether in a yield of only 57% (corresponds to a TON of 2 000). The n/iso ratio of product 1 to product 2 was in this case only 3.75:1. In a further patent by National Distillers, the product mixture was separated from the reaction solution by extraction with hexane. The telomerization was carried out in dimethylformamide or sulfolane using a catalyst mixture of palladium(II) acetate/3 equivalents of triphenylphosphinemonosulfonate. The first batch gave the linear telomer with a TON of 900. The selectivity to the linear alcohol was a low 40%.

Longer-chain primary alcohols such as ethanol, propanol and butanol (J. Beger, H. Reichel, *J. Prakt. Chem.* 1973, 315, 1067) also form the corresponding telomers with butadiene. However, the catalyst activity of the known catalysts is in these cases even lower than in those mentioned above. Thus, identical reaction conditions [Pd(acetylacetonate)$_2$/PPh$_3$/butadiene/alcohol=1:2:2 000:5 000; 60° C./10 h] result in formation of the telomers of methanol in a yield of 88%, those of propanol in a yield of 65% and those of nonanol in a yield of only 21%.

In summary, it can be said that the known palladium-phosphine catalysts for telomerization reactions of butadiene with alcohols do not give satisfactory catalytic turnover numbers (=TONs). TONs of >100 000 as are sought in industry have rarely been described for known systems. At the same time, it is desirable to achieve high selectivities of >95% chemoselectivity and regioselectivity in order to obtain an ecologically advantageous process.

Like alcohols, carboxylic acids are suitable nucleophiles in telomerization reactions. Acetic acid and butadiene give good yields of the corresponding octadienyl derivatives 1a, 1b and 2 in which R=Me-CO, X=O (DE 2 137 291). The ratio of the products 1/2 can be influenced via the ligands on the palladium (D. Rose, H. Lepper, *J. Organomet. Chem.* 1973, 49; 473). Use of triphenylphosphine as ligand gave a ratio of 4/1, while use of tris(o-methylphenyl) phosphite enabled the ratio to be increased to 17/1. Other carboxylic acids such as pivalic acid, benzoic acid or methacrylic acid, and also dicarboxylic acids, can likewise be reacted with butadiene.

In U.S. Pat. No. 5,030,792, Shell Oil has described a process for preparing α-olefins which is based on the telomerization of conjugated dienes by means of carboxylic acids.

Telomerization reactions in which water is used as nucleophile have been intensively studied by, inter alia, Kuraray (U.S. Pat. Nos. 4,334,117, 4,356,333, 5,057,631). Here, phosphines, mostly water-soluble phosphines, or phosphonium salts (EP 0 296 550) are used as ligands. The use of water-soluble diphosphines as ligands is described in WO 98 08 794, while DE 195 23 335 claims the reaction of alkadienes with water in the presence of phosphonite or phosphinite ligands.

The telomerization of butadiene by means of nucleophiles such as formaldehyde, aldehydes, ketones, carbon dioxide, sulfur dioxide, sulfinic acids, β-keto esters, β-diketones, malonic esters, α-formylketones and silanes has likewise been described.

The major part of the work on telomerization has been carried out using butadiene. However, the reaction is also applicable to other dienes having conjugated double bonds. These can formally be regarded as derivatives of butadiene in which the hydrogen atoms are replaced by other groups. Isoprene is of particular industrial importance. Since isoprene is, unlike butadiene, an unsymmetrical molecule, telomerization results in the formation of further isomers (J. Beger, Ch. Duschek, H. Reichel, *J. Prakt. Chem.* 1973, 315, 1077–89). The ratio of these isomers is influenced to a considerable extent by the type of nucleophile and the choice of ligands.

Owing to the stated importance of telomerization products and the problems associated with the prior art, there is a great need for new catalyst systems for telomerization reactions, which have inexpensive stable ligands, which do not display the disadvantages of the known catalytic processes, which are suitable for industrial implementation and which give the telomerization products in high yield, with high catalyst productivity and in high purity.

This object is achieved by a process for the telomerization of acyclic olefins having at least two conjugated double bonds (I) or mixtures comprising such olefins by means of nucleophiles (II) using a palladium-carbene complex as catalyst.

In a preferred embodiment, the nucleophiles (II) used are compounds of the formula (IIa) or (IIb),

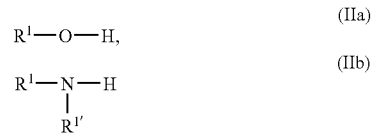

where $R^1$, $R^{1'}$ are selected independently from among hydrogen, linear, branched or cyclic $C_1$–$C_{22}$-alkyl groups, alkenyl groups, alkynyl groups, the carboxyl group and $C_6$–$C_{18}$-aryl groups, where these groups may bear substituents selected from the group consisting of —CN, —COOH, —COO-alkyl-($C_1$–$C_8$), —CO-alkyl-($C_1$–$C_8$), -aryl-($C_6$–$C_{10}$), —COO-aryl-($C_6$–$C_{10}$), —CO-aryl-($C_6$–$C_{10}$), —O-alkyl-($C_1$–$C_8$), —O—CO-alkyl-($C_1$–$C_8$), —N-alkyl$_2$-($C_1$–$C_8$), —CHO, —SO$_3$H, —NH$_2$, —F, —Cl, —OH, —CF$_3$, —NO$_2$, and the radicals $R^1$, $R^{1'}$ may be joined to one another via covalent bonds.

The catalyst used is preferably a palladium complex comprising carbene ligands of the formula (III) or (IV)

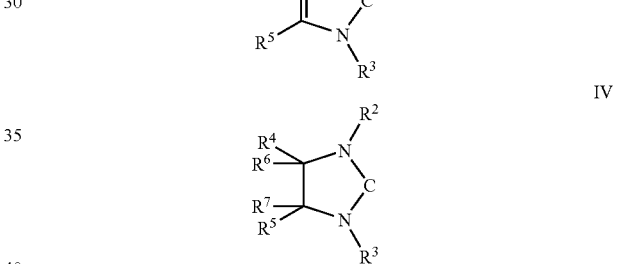

where $R^2$ and $R^3$ are each, independently of one another, a linear, branched or cyclic $C_1$–$C_{24}$-alkyl or $C_5$–$C_{18}$-aryl group and the alkyl and aryl groups may, independently of one another, bear the substituents —CN, —COOH, COO-alkyl-($C_1$–$C_8$), —CO-alkyl-($C_1$–$C_8$), -aryl-($C_5$–$C_{18}$), -alkyl-($C_1$–$C_{24}$), —COO-aryl-($C_6$–$C_{10}$), —CO-aryl-($C_6$–$C_{10}$), —O-alkyl-($C_1$–$C_8$), —O—CO-alkyl-($C_1$–$C_8$), —N-alkyl$_2$—($C_1$–$C_8$), —CHO, —SO$_3$H, —NH$_2$, -F, —Cl, —OH, —CF$_3$, —NO$_2$, ferrocenyl, and $R^4$ to $R^7$ are each, independently of one another, hydrogen, —CN, —COOH, —COO-alkyl-($C_1$–$C_8$), —CO-alkyl-($C_1$–$C_8$), —COO-aryl-($C_6$–$C_{10}$), —CO-aryl-($C_6$–$C_{10}$), —O-alkyl-($C_1$–$C_8$), —O—CO-alkyl-($C_1$–$C_8$), —N-alkyl$_2$-($C_1$–$C_8$), —CHO, —SO$_3$H, —NH$_2$, —F, —Cl, —OH, —CF$_3$, —NO$_2$ or a linear, branched or cyclic $C_1$–$C_{24}$-alkyl or $C_6$–$C_{18}$-aryl group and the alkyl and aryl groups may, independently of one another, bear the substituents —CN, —COOH, —COO-alkyl-($C_1$–$C_8$), —CO-alkyl-($C_1$–$C_8$), -aryl-($C_6$–$C_{10}$), —COO-aryl-($C_6$–$C_{10}$), —CO-aryl-($C_6$–$C_{10}$), —O-alkyl-($C_1$–$C_8$), —O—CO-alkyl-($C_1$–$C_8$), —N-alkyl$_2$-($C_1$–$C_8$), —CHO, —SO$_3$H, —NH$_2$, —F, —Cl, —OH, —CF$_3$, —NO$_2$, where the radicals $R^4$ and $R^5$ may also be part of a bridging aliphatic or aromatic ring.

In the telomerization, it is in principle possible to use all acyclic olefins having at least two conjugated double bonds.

For the purposes of the present invention, the use of 1,3-butadiene and isoprene (2-methyl-1,3-butadiene) is preferred. It is possible to use both the pure dienes and mixtures in which these dienes are present.

As 1,3-butadiene-containing mixtures, preference is given to using mixtures of 1,3-butadiene with other $C_4$-hydrocarbons and/or $C_5$-hydrocarbons. Such mixtures are obtained, for example, in cracking processes for the production of ethene, in which refinery gases, naphtha, gas oil, LPG (liquefied petroleum gas), NGL (natural gas liquid), etc., are used as feedstocks. The $C_4$ fractions obtained as by-product in these processes comprise, depending on the cracking process, variable amounts of 1,3-butadiene. Typical 1,3-butadiene concentrations in the $C_4$ fraction obtained from a naphtha steam cracker are 20–70% of 1,3-butadiene.

The $C_4$ components n-butane, i-butane, 1-butene, cis-2-butene, trans-2-butene and i-butene which are likewise present in these fractions do not interfere significantly with the reaction in the telomerization step.

In contrast, dienes having cumulated double bonds (1,2-butadiene, allene, etc.) and alkynes, in particular vinylacetylene, can act as moderators in the telomerization reaction. It is therefore advantageous for the $C_4$-alkynes and, if appropriate, the 1,2-butadiene to be removed beforehand (DE 195 23 335). This can, if possible, be carried out by means of physical processes such as distillation or extraction. A possible chemical route is selective hydrogenation to convert the alkynes into alkenes or alkanes and the cumulated dienes into monoenes. Processes for such hydrogenations are prior art and are described, for example, in WO 98/12160, EP-A-0 273 900, DE-A-37 44 086 or U.S. Pat. No. 4,704,492.

As nucleophiles, preference is given to using any compounds which have the formula II. Examples of telogens of the formula II are
water,
monoalcohols and phenols such as methanol, ethanol, n-propanol, isopropanol, allyl alcohol, butanol, octanol, 2-ethylhexanol, isononanol, benzyl alcohol, cyclohexanol, cyclopentanol, 2-methoxyethanol, phenol or 2,7-octadien-1-ol,
dialcohols such as ethylene glycol, 1,2-propanediol, 1,3-propanediol, 1,4-butanediol, 1,2-butanediol, 2,3-butanediol and 1,3-butanediol,
polyols such as glycerol, glucose, sucrose,
hydroxy compounds such as α-hydroxyacetic esters,
carboxylic acids such as acetic acid, propanoic acid, butanoic acid, isobutanoic acid, benzoic acid, 1,2-benzenedicarboxylic acid, 1,3-benzenedicarboxylic acid, 1,4-benzenedicarboxylic acid, 1,2,4-benzenetricarboxylic acid,
ammonia,
primary amines such as methylamine, ethylamine, propylamine, butylamine, octylamine, 2,7-octadienylamine, dodecylamine, aniline, ethylenediamine or hexamethylenediamine,
secondary amines such as dimethylamine, diethylamine, N-methylaniline, bis(2,7-octadienyl)amine, dicyclohexylamine, methylcyclohexylamine, pyrrolidine, piperidine, morpholine, piperazine or hexamethylenimine.

Telogens which can themselves be obtained via a telomerization reaction can be introduced directly or else formed in situ. Thus, for example, 2,7-octadien-1-ol can be formed in situ from water and butadiene in the presence of the telomerization catalyst, 2,7-octadienylamine can be obtained from ammonia and 1,3-butadiene, etc.

Particularly preferred telogens are water, methanol, ethanol, n-butanol, allyl alcohol, 2-methoxyethanol, phenol, ethylene glycol, 1,3-propanediol, glycerol, glucose, sucrose, acetic acid, butanoic acid, 1,2-benzene-dicarboxylic acid, ammonia, dimethylamine and diethylamine.

As solvents, use is generally made of the nucleophile employed in the reaction, provided that it is liquid under the reaction conditions. However, other solvents can also be used. The solvents used should be largely inert. The addition of solvents is preferred when using nucleophiles which are solid under the reaction conditions or in the case of products which would be obtained as solids under the reaction conditions. Suitable solvents include aliphatic, cycloaliphatic and aromatic hydrocarbons such as $C_3$–$C_{20}$-alkanes, mixtures of lower alkanes ($C_3$–$C_{20}$), cyclohexane, cyclooctane, ethylcyclohexane, alkenes and polyenes, vinylcyclohexene, 1,3,7-octatriene, the $C_4$-hydrocarbons from $C_4$ fractions from crackers, benzene, toluene and xylene; polar solvents such as tertiary and secondary alcohols, amides such as acetamide, dimethylacetamide and dimethylformamide, nitriles such as acetonitrile and benzonitrile, ketones such as acetone, methyl isobutyl ketone and diethyl ketone; carboxylic esters such as ethyl acetate, ethers such as dipropyl ether, diethyl ether, dimethyl ether, methyl octyl ether, 3-methoxyoctane, dioxane, tetrahydrofuran, anisole, alkyl and aryl ethers of ethylene glycol, diethylene glycol and polyethylene glycol and other polar solvents such as sulfolane, dimethyl sulfoxide, ethylene carbonate, propylene carbonate and water. Ionic liquids, for example imidazolium or pyridinium salts, can also be used as solvents.

The solvents are used either alone or as mixtures of various solvents.

The temperature at which the telomerization reaction is carried out is in the range from 10 to 180° C., preferably from 30 to 120° C., particularly preferably from 40 to 100° C. The reaction pressure is from 1 to 300 bar, preferably from 1 to 120 bar, particularly preferably from 1 to 64 bar and very particularly preferably from 1 to 20 bar.

An essential feature of the process of the invention is that the telomerization reaction is carried out using catalysts based on palladium complexes comprising carbene ligands.

Examples of carbene ligands of the formula III or IV and complexes in which such ligands are present have been described in the technical literature (W. A. Herrmann, C. Köcher, *Angew. Chem.* 1997, 109, 2257; Angew. Chem. Int. Ed. Engl. 1997, 36, 2162; V. P. W. Böhm, C. W. K. Gstöttmayr, T. Weskamp, W. A. Herrmann, *J. Organomet. Chem.* 2000, 595, 196; DE 44 47 066).

For the purposes of the present invention, the term carbene ligands encompasses both free carbenes which can function as ligand and carbenes coordinated to palladium.

The catalyst metal palladium from which the active catalysts are formed under the reaction conditions can be introduced into the process in various ways.

a) As palladium-carbene complexes in which the palladium is preferably present in the oxidation state (II) or (0).
b) In the form of palladium precursors from which the catalysts are formed in situ.

In the case of a):
Examples are palladium(0)-carbene-olefin complexes, palladium(0)-dicarbene complexes and palladium(II)-dicarbene complexes, palladium(0)-carbene-1,6-diene complexes. Compounds which can function as 1,6-diene are, for example, diallylamine, 1,1'-divinyltetramethyldisiloxane, 2,7-octadienyl ether or 2,7-octadienylamines. Further examples are shown in the formulae I-a to I-e below.

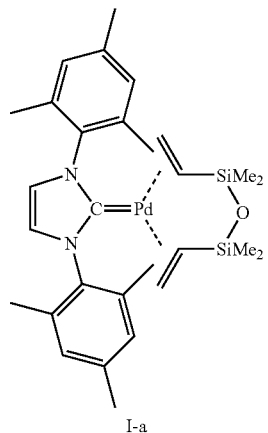
I-a
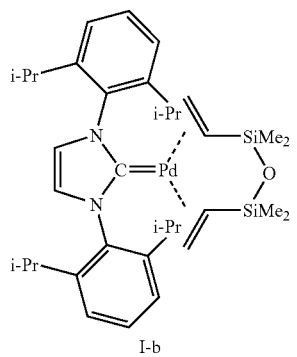
I-b
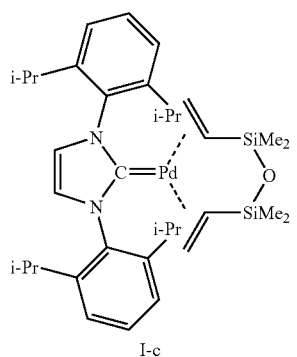
I-c
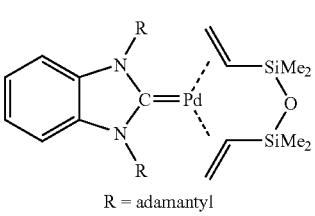
R = adamantyl
I-d
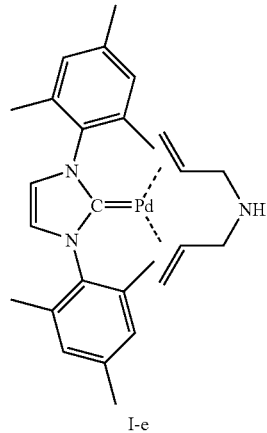
I-e
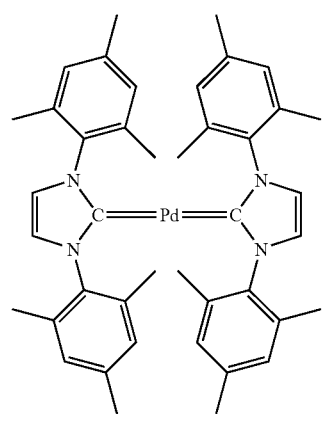
I-f
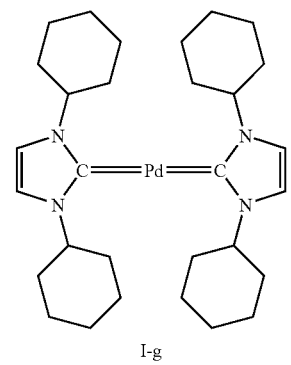
I-g
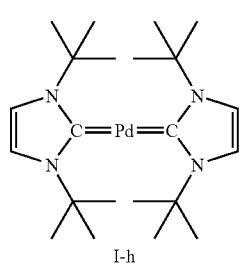
I-h -continued

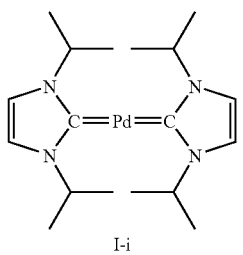

I-i

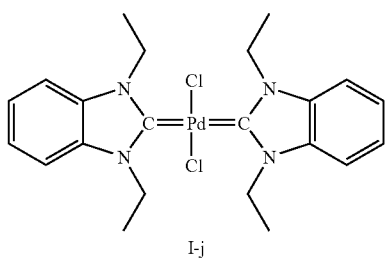

I-j

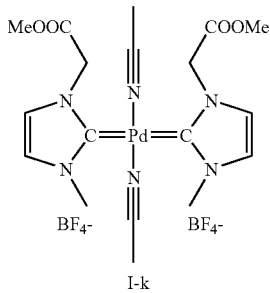

I-k

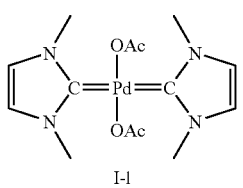

I-l

The carbene complexes of palladium can be prepared in various ways. A simple route is, for example, the addition of carbene ligands or the replacement of ligands on palladium complexes by carbene ligands. Thus, for example, the complexes I-f to I-i are obtainable by replacement of the phosphorus ligands of the complex bis(tri-o-tolylphosphine)palladium(0) (T. Weskamp, W. A. Herrmann, *J. Organomet. Chem.* 2000, 595, 186).

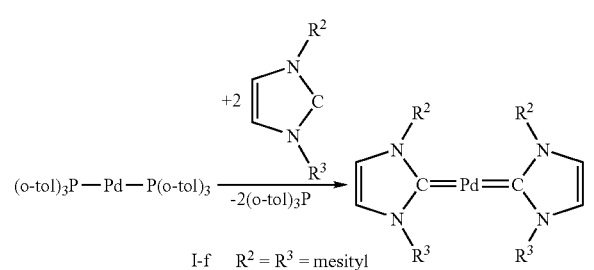

I-f  $R^2 = R^3 = $ mesityl
I-g  $R^2 = R^3 = $ c-hexyl
I-h  $R^2 = R^3 = $ t-butyl
I-i  $R^2 = R^3 = $ i-propyl In the case of b):

Palladium precursors which can be used are, for example: palladium(II) acetate, palladium(II) chloride, palladium(II) bromide, lithium tetrachloropalladate, palladium(II) acetylacetonate, palladium(0)-dibenzylideneacetone complexes, palladium(II) propionate, bis(acetonitrile)palladium(II) chloride, bis(triphenylphosphine)palladium(II) dichloride, bis(benzonitrile)palladium(II) chloride, bis(tri-o-tolylphosphine)palladium(0) and further palladium(0) and palladium (II) complexes.

The carbenes of the formulae III and IV are used in the form of free carbenes or as metal complexes or are generated in situ from carbene precursors.

Suitable carbene precursors are, for example, salts of the carbenes which have the formulae V and VI,

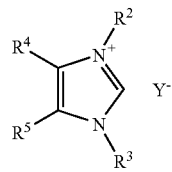

V

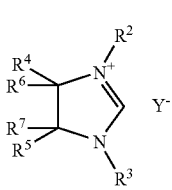

VI where $R^2$, $R^3$, $R^4$, $R^5$, $R^6$, $R^7$ are as defined in the formulae III and IV and Y is a singly charged anionic group or a fraction corresponding to the stoichiometry of a multiply charged anionic group.

Examples of Y are halides, hydrogensulfate, sulfate, alkylsulfates, arylsulfates, borates, hydrogencarbonate, carbonate, alkylcarboxylates, arylcarboxylates.

The corresponding carbenes can be liberated from the salts of the carbenes by, for example, reaction with a base.

The concentration of the catalyst, indicated formally in ppm (by mass) of palladium metal based on the total mass, is from 0.01 ppm to 1 000 ppm, preferably from 0.5 to 100 ppm, particularly preferably from 1 to 50 ppm.

The ratio [mol/mol] of carbene to Pd is from 0.01:1 to 250:1, preferably from 1:1 to 100:1, particularly preferably from 1:1 to 50:1. Apart from the carbene ligands, further ligands such as phosphorus ligands, e.g. triphenylphosphine, may be present in the reaction mixture.

Due to the catalyst activities and stabilities, it is possible to use extremely small amounts of catalyst in the process of the invention. Apart from a process in which the catalyst is reused, it is therefore also an option not to recycle the catalyst. Both variants have been described in the patent literature (WO 90/13531, U.S. Pat. No. 5,254,782, 4,642, 392).

It is often advantageous to carry out the telomerization reaction in the presence of bases. Preference is given to using basic components having a $pK_b$ of less than 7, in particular compounds selected from the group consisting of amines, alkali metal salts and alkaline earth metal salts.

Examples of suitable basic components are amines such as trialkylamines which may be alicyclic or/and open-chain, amides, alkali metal or/and alkaline earth metal salts of aliphatic or/and aromatic carboxylic acids, e.g. acetates, propionates or benzoates, or appropriate carbonates, hydrogen carbonates, alkoxides of alkali metals and/or alkaline earth metals, phosphates, hydrogenphosphates or/and hydroxides, preferably of lithium, sodium, potassium, calcium, magnesium, cesium, ammonium and phosphonium compounds. Preferred additives are hydroxides of the alkali metals and alkaline earth metals and metal salts of the nucleophile of the formula II.

The basic component is generally used in an amount of from 0.01 mol % to 10 mol % (based on the olefin), preferably from 0.1 mol % to 5 mol % and very particularly preferably from 0.2 mol % to 1 mol %.

In the process of the invention, the ratio [mol/mol] of diene used and nucleophile is from 1:100 to 100:1, preferably from 1:50 to 10:1, particularly preferably from 1:10 to 2:1.

The process of the invention can be carried out continuously or batchwise and is not restricted to the use of particular types of reactor. Examples of reactors in which the reaction can be carried out are stirred tank reactors, cascades of stirred tanks, flow tubes and loop reactors. Combinations of various reactors are also possible, for example a stirred tank reactor together with a downstream flow tube.

In the process of the invention, carbene ligands are used in telomerization reactions for the first time. Surprisingly, the catalysts used according to the invention are superior to the known palladium-phosphine catalysts both in respect of selectivity and in respect of productivity. In the process of the invention, it is possible, for example, to achieve turnover values for the catalysts (catalyst productivities) in the order of 200 000 and more without problems in the telomerization of butadiene by means of alcohols.

The following examples illustrate the invention without restricting the scope of the patent application.

EXAMPLES

General Procedure for the Telomerization of Butadiene By Means of Methanol:

In a 100 ml Schlenk tube, an appropriate amount of catalyst (from 0.01 to 0.0001 mol %) is dissolved in 56 g (1.75 mol) of methanol under protective gas. The solution is admixed with 5 mmol of triethylamine or sodium hydroxide. The reaction solution is subsequently drawn into the evacuated autoclave, the autoclave is cooled to T<−10° C. and butadiene is condensed in (amount determined by means of the decrease in mass of the butadiene stock bottle). The autoclave is heated to the reaction temperature, and after the reaction is cooled to room temperature. Unreacted butadiene is condensed in a cold trap cooled by means of dry ice. The conversion is determined from the increase in mass of the reaction solution. To isolate the product, the solution is distilled under reduced pressure.

GC analysis: The reaction solution was admixed with 5 ml of isooctane (a) or 5 ml of diethylene glycol dimethyl ether (b) (GC standard).

2,7-Octadien-1-yl methyl ether:

GC (column HP 5/30 m, temp. program: 35° C., 10 min, at 8° C. min$^{-1}$ to 280° C., inj.: 250° C., const. flow, a). $t_R$(vinylcyclohexene)=12.3 min, $t_R$(octatriene)=11.6 min and 11.7 min, $t_R$(1)=19 min, $t_R$(isooctane)= 4.5 min.

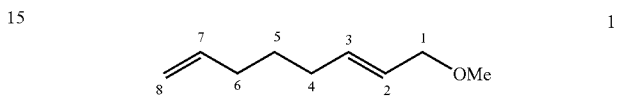

$^1$H NMR (CDCl$_3$, 400 MHz) δ=1.39 (quint, $^3J_{5, 4\ and\ 6}$=8 Hz, 2H, 5-H), 1.9 (m, 4H, 4-H and 6-H), 3.2 (s, 3H, OCH$_3$), 3.7 (d, $^3J_{1,\ 2}$=6 Hz, 2H, 1-H), 4.75–4.9 (m, 2H, 8-H), 5.35–5.45 (m, 1H, 7-H), 5.5–5.7 (m, 2H, 2-H and 3-H). $^{13}$C NMR (CDCl$_3$, 100 MHz): δ=28.6 (C-5), 32.0 (C-4), 33.5 (C-6), 57.9 (OCH$_3$), 73.5 (C-1), 114.9 (C-8), 126.9 (C-2), 134.8 (C-3), 138.8 (C-7).

2,7-Octadien-1-yl butyl ether:

GC (column HP 5/30 m, temp. program: 35° C., 10 min, at 8° C. min$^{-1}$ to 280° C., inj.: 250° C., const. flow, b). $t_R$(vinylcyclohexene)=12 min, $t_R$(octatriene)=11.6 min and 11.7 min, $t_R$(2) 24.1 min, $t_R$(diglyme)=17.1 min.

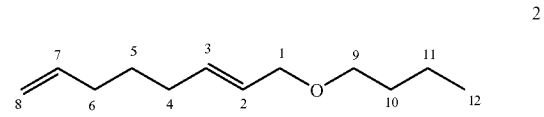

1H NMR (CDCl$_3$, 400 MHz): δ=0.75 (t, J=7.3 Hz, 3H, 12-H), 1.25 (sext, J=7.1 Hz, 2H, 11-H), 1.39 (q, $^3J_{5, 4\ and\ 6}$=7 Hz, 2H, 5-H), 1.42 (quint, J=7.1 Hz, 2H, 10-H), 1.9 (m, 4H, 4-H and 6-H), 3.26 (t, J=6.7 Hz, 2H, 9-H), 3.7 (dd, J=6 Hz, J=1 Hz, 2H, 1 4.764.9 (m, 2H, 8-H), 5.36–5.45 (m, 1H, 7-H), 5.5–5.7 (m, 2H, 2-H and 3-H). $^{13}$C NMR (CDCl$_3$, 100 MHz): δ=13.6 (C-12), 19.1 (C-11), 28.05 (C-5), 31.4 (C-10), 31.6 (C-4), 32.9 (C-6), 69.1 (C-9), 71.3 (C-1), 114.3 (C-8), 126.7 (C-2), 133.5 (C-3), 138.2 (C-7).

MS m/e (%): 182 [M$^+$] (1.4), 139 (4.3), 126 (10.6), 108 (24), 101 (3.9), 97 (11), 93 (27), 82 (35), 67 (72), 57 (100); HRMS: calculated for C$_{12}$H$_{22}$O: 182.16707, found: 182.16460

Experimental Examples 1–17

The telomerization was carried out by a method analogous to the general procedure for the telomerization of butadiene using methanol as alcohol. When using other alcohols, the mass of alcohol was maintained and the amounts of butadiene, catalyst, etc., were modified as shown in the table. As palladium compounds, the complexes A-E were added. The base used was sodium hydroxide, and the reaction time was in each case 16 hours.

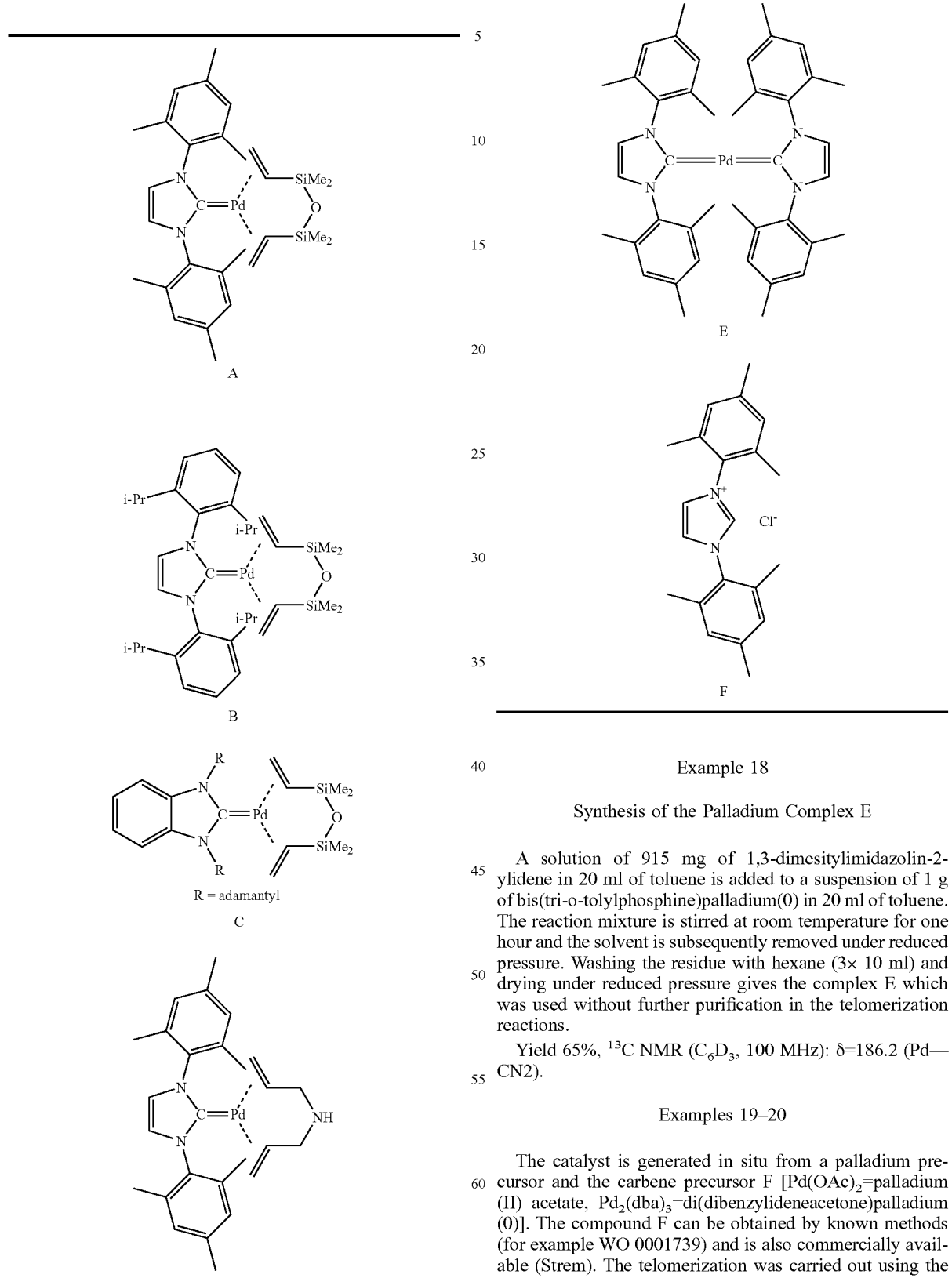

Example 18

Synthesis of the Palladium Complex E

A solution of 915 mg of 1,3-dimesitylimidazolin-2-ylidene in 20 ml of toluene is added to a suspension of 1 g of bis(tri-o-tolylphosphine)palladium(0) in 20 ml of toluene. The reaction mixture is stirred at room temperature for one hour and the solvent is subsequently removed under reduced pressure. Washing the residue with hexane (3× 10 ml) and drying under reduced pressure gives the complex E which was used without further purification in the telomerization reactions.

Yield 65%, $^{13}C$ NMR ($C_6D_3$, 100 MHz): δ=186.2 (Pd—CN2).

Examples 19–20

The catalyst is generated in situ from a palladium precursor and the carbene precursor F [Pd(OAc)$_2$=palladium (II) acetate, Pd$_2$(dba)$_3$=di(dibenzylideneacetone)palladium (0)]. The compound F can be obtained by known methods (for example WO 0001739) and is also commercially available (Strem). The telomerization was carried out using the general procedure for the telomerization of butadiene by means of methanol. The base used was sodium hydroxide, and the reaction time was in each case 16 hours.

| No. | Nucleophile | Nu/butadiene [mol/mol] | Catalyst | Pd [mol %] | Base [mol %] | Temp. [° C.] | n + iso telomer [%] | n:iso [%]:[%] | OT + OD + VCH [%] | TON |
|---|---|---|---|---|---|---|---|---|---|---|
| 1 | MeOH | 1:2 | A | 0.01 | 1 | 90 | ≧98 | 96.5:3.5 | 1.8 | >9 800 |
| 2 | MeOH | 1:2 | A | 0.001 | 1 | 90 | ≧98 | 97.3:2.7 | 1.2 | >98 000 |
| 3 | MeOH | 1:2 | A | 0.001 | 1 | 50 | 56.5 | 98.8:1.2 | — | 56 500 |
| 4 | MeOH | 1:2 | A | 0.0003 | 1 | 90 | 77 | 98:2 | 1.8 | 256 667 |
| 5 | BuOH | 1:2 | A | 0.001 | 1 | 90 | 91 | 98.1:1.9 | 3.5 | 91 000 |
| 6 | BuOH | 1:2 | A | 0.0003 | 1 | 90 | 70 | 97.2:2.8 | 4.2 | 233 333 |
| 7 | EtOH | 1:2 | A | 0.0003 | 1 | 90 | 75 | 97:3 | 2.4 | 250 000 |
| 8 | MeOH | 1:1 | A | 0.001 | 1 | 70 | 87 | 98.2:1.8 | 0.8 | 87 000 |
| 9 | 2-EHOH | 1:2 | A | 0.0003 | 1 | 90 | 87 | 99:1 | 1.8 | 290 000 |
| 10 | MeOH | 1:2 | B | 0.0003 | 1 | 90 | 81 | 98.2:1.8 | 1.5 | 270 000 |
| 11 | MeOH | 1:2 | C | 0.0003 | 1 | 90 | 90 | 97.2:2.8 | 2.2 | 300 000 |
| 12 | MeOH | 1:2 | D | 0.0003 | 1 | 90 | 75 | 97.5:2.5 | 2.4 | 250 000 |
| 13 | MeOH | 1:2 | Pd(OAc)$_2$/3PPh$_3$ | 0.001 | 1 | 90 | 79 | 92.2:7.8 | 9.2 | 79 000 |
| 14 | MeOH | 1:2 | Pd(OAc)$_2$/3PPh$_3$ | 0.0003 | 1 | 90 | 74 | 93:7 | 9.5 | 246 666 |
| 15 | BuOH | 1:2 | Pd(OAc)$_2$/3PPh$_3$ | 0.001 | 1 | 90 | 16.7 | 94:6 | 31.2 | 16 700 |
| 16 | MeOH | 1:2 | E | 0.001 | 1 | 90 | 90 | 97.4:2.6 | 1.8 | 90 000 |
| 17 | MeOH | 1:2 | E | 0.0003 | 1 | 90 | 76.3 | 97.6:2.4 | 2.5 | 254 000 |
| 19 | MeOH | 1:2 | Pd(OAc)$_2$/3 F | 0.001 | 1 | 90 | 86 | 97.3:2.7 | 1.3 | 86 000 |
| 20 | MeOH | 1:2 | Pd(dba)/3 F | 0.001 | 1 | 90 | 94.7 | 97.2:2.8 | 1.5 | 94 700 |

Nu = nucleophile
OT = octatriene
n + iso = sum of product 1 + 2
OD = octadiene
n:iso = ratio of product 1 to 2
VCH = vinylcyclohexene
TON = turnover number Examples 21–22

In a 100 ml Schlenk tube, 70.6 g (0.75 mol) of phenol and the appropriate amount of the catalyst A (mol % of Pd based on mol of butadiene) are dissolved in 70 ml of tetrahydrofuran under protective gas. As base, sodium phenoxide is added, 1 mol % based on the amount of phenol used. The reaction solution is subsequently drawn into the evacuated autoclave, the autoclave is cooled to T<−10° C. and butadiene is condensed in (amount determined by means of the decrease in mass of the butadiene stock bottle). The molar ratio of phenol to butadiene was 2:1.

The autoclave is heated to 90° C. and after 16 hours cooled to room temperature. Unreacted butadiene is condensed in a cold trap cooled by means of dry ice. The conversion is determined from the increase in mass of the reaction solution. To isolate the product, the solution is distilled under reduced pressure.

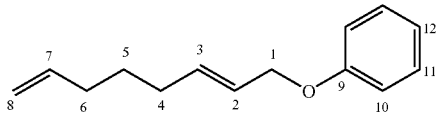

Example 23

The telomerization was carried out by a method analogous to the general procedure for the telomerization of butadiene by means of methanol. The complex A was added as palladium compound. The base used was sodium isopropoxide, 1 mol %. The reaction time was 16 hours at 90° C., and the molar ratio of i-propanol to butadiene was 2:1.

| No. | Base | Pd [mol %] | n + iso telomer [%] | n:iso [%]:[%] | OT + VCH [%] | TON |
|---|---|---|---|---|---|---|
| 21 | NaOPh | 0.005 | 56 | 89:11 | 1.3 | 11 200 |
| 22 | NaOPh | 0.001 | 6.4 | 95:5 | 3.4 | 6 400 |

| No. | Catalyst | Pd [mol %] | n + iso telomer [%] | n:iso [%]:[%] | OT + VCH [%] | TON |
|---|---|---|---|---|---|---|
| 23 | A | 0.005 | 72.5 | 82:18 | 26.5 | 14 500 |

2,7-Octadien-1-yl phenyl ether:

$^1$H NMR (CDCl$_3$, 400 MHz) δ=1.8 (quin, J=7.5, 5-H), 2.3–2.4 (m, 4H, 4-H and 6-H), 4.74 (d,d, J=5.5, J=1, 2H, 1-H), 5.2–5.35 (m, 2H, 8-H), 5.9–6.2 (m, 3H, 7-H, 2-H, 3-H) 7.18–7.21 (m, 3H, 10-H, 12-H), 7.5–7.6 (m, 2H, 11-H) $^{13}$C NMR (CDCl$_3$, 100 MHz): δ=28.0 (C-5), 31.6 (C4), 33.0 (C-6), 68.4 (C-1), 114.53 (C-8), 120.5 (C-11), 125.1 (C-2), 129.1 (C-12), 129.2 (C-10), 134.8 (C-3), 138.3 (C-7), 158.5 (C-9)

MS m/e (%): [M$^+$] 202 (2.5), 108 (9.9), 94 (100), 79 (11), 67 (55), 58 (11) 55 (24), 43 (40), HRMS: calculated for C$_{14}$H$_{18}$O: 202.13577, found: 202.13485

2,7-Octadien-1-yl isopropyl ether:

GC (column HP 5/30 m, temp. program: 35° C., 10 min, at 8° C. min$^{-1}$ to 280° C., inj.: 250° C., const. flow, b). t$_R$(vinylcyclohexene)=12 min, t$_R$(octatriene)=11.6 min and 11.7 min, t$_R$(2)=19.2 min, t$_R$(1)=16.51, t$_R$(diglyme)=17.1 min.

$^1$H NMR (CDCl$_3$, 400 MHz) δ=1.05 (d of s, 6H, 10-H, 11-H), 1.4 (quint, J=7.5 Hz, 2H, 10-H), 1.9 (m, 4H, 4-H and 6-H), 3.5 (sept, J=6.1 Hz, 2H, 9-H), 3.82 (dd, J=6.2 Hz, J=1 Hz, 2H, 1-H), 4.76–4.9 (m, 2H, 8-H), 5.36–5.45 (m, 1H, 7-H), 5.5–5.75 (m, 2H, 2-H and 3-H).

$^{13}$C NMR (CDCl$_3$, 100 MHz): δ=21.7 (C-11, C-10), 27.9 (C-5), 31.3 (C-4), 32.9 (C-6), 69.1 (C-9), 70.8 (C-1), 114.8 (C-8), 127.7 (C-2), 133.5 (C-3), 138.7 (C-7).

MS m/e (%): [M$^+$] 168 (0.11), 126 (12.5), 109 (30.6), 97 (13), 93 (25), 82 (68), 67 (95), 55 (76), 43 (100)

EA: calculated for $C_{11}H_{20}O$: C: 78.51, H: 11.98, found: C: 78.56, H: 11.95

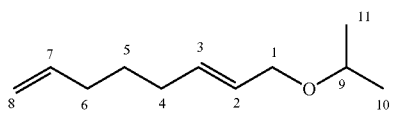

Example 24

Synthesis of 1,3-bis(2,4,6-trimethylphenyl)imidazolium tosylate (G)

A solution of 1.5 g (4.4 mmol) of 1,3-bis(2,4,6-trimethylphenyl)imidazolium chloride (F) in 10 ml of absolute MeOH is admixed with 0.854 g (4.4 mmol) of sodium tosylate. After the sodium tosylate has dissolved completely (magnetic stirring), the solution is evaporated under reduced pressure to a volume of about 3 ml, after which 50 ml of acetone are added. The mixture is stirred at 40° C. for two hours, the precipitated sodium chloride is filtered off and the solution is evaporated under reduced pressure to about 10 ml. After 24 hours, the white crystals which have precipitated are filtered off and washed with 5 ml of acetone and dried under reduced pressure. The yield is 1.9 g (90%). M=476.63 g/mol. This method of double decomposition can be used to replace the chloride anion by various other anions, for example carboxylate anions.

$^1$H-NMR (δ[ppm], J[Hz], MeOH-d$_4$): 2.17 s (12H), 2.29 s (3H), 2.34 s (6H), 3.92 s (2H), 7.1 d (2H, J=8.5), 7.13 s (4H), 7.6 d (2H, J=8.5), 8.1 s (2H) $^{13}$C-NMR (δ[ppm], MeOH-d$_4$): 143.1 s, 140.4 s, 138.1 s, 133.6 s, 130.1 s, 128.6 s, 127.3 s, 124.9 s, 124.1 s

Examples 25–28

The telomerization was carried out by a method analogous to the general procedure for the telomerization of butadiene by means of methanol. 15.0 g of 1,3-butadiene, 17.8 g of methanol, 0.00127 g of tris(dibenzylideneacetone)dipalladium(0) and 0.11 g of sodium hydroxide were used in each case. Ligands used were 1,3-bis(2,4,6-trimethylphenyl)imidazolium chloride (F) and 1,3-bis(2,4,6-trimethylphenyl)imidazolium tosylate (G). Reactions were carried out at 50° C. and 90° C., and the reaction time was in each case 16 hours.

| No. | Ligand | Ligand/Pd [mol/mol] | Temp. [° C.] | Yield of n + iso telomer [%] | N:iso [%]:[%] | Yield of OT + VCH [%] |
|---|---|---|---|---|---|---|
| 25 | F | 4/1 | 50 | 29.6 | 98.5:1.5 | 0.3 |
| 26 | G | 4/1 | 50 | 35.0 | 98.5:1.5 | 0.3 |
| 27 | F | 2/1 | 90 | 94.3 | 97.5:2.5 | 1.4 |
| 28 | G | 2/1 | 90 | 92.0 | 97.6:2.4 | 1.0 |

What is claimed is:

1. A process for the telomerization of acyclic olefins, comprising: reacting acyclic olefins having at least two conjugated double bonds (I) or mixtures comprising said acyclic olefins with nucleophiles (II) in the presence of a palladium-carbene complex catalyst.

2. The process as claimed in claim 1, wherein the nucleophiles are compounds selected from the group consisting of water, alcohols, phenols, polyols, carboxylic acids, ammonia and primary and secondary amines.

3. The process as claimed in claim 1, wherein the nucleophiles (II) are compounds of formula (IIa) or (IIb),

where $R^1$, $R^{1'}$ are selected independently from the group consisting of hydrogen, linear, branched or cyclic $C_1$–$C_{22}$-alkyl groups, alkenyl groups, alkynyl groups, the carboxyl group and $C_5$–$C_{18}$-aryl groups, where these groups optionally bear substituents selected from the group consisting of —CN, —COOH, —COO-alkyl-($C_1$–$C_8$), —CO-alkyl-($C_1$–$C_8$), -aryl-($C_5$–$C_{10}$), —COO-aryl-($C_6$–$C_{10}$), —CO-aryl-($C_6$–$C_{10}$), —O-alkyl-($C_1$–$C_8$), —O—CO-alkyl-($C_1$–$C_8$), —N-alkyl$_2$-($C_1$–$C_8$), —CHO, —SO$_3$H, —NH$_2$, —F, —Cl, —OH, —CF$_3$, —NO$_2$, and the radicals $R^1$, $R^{1'}$ optionally are joined to one another via covalent bonds.

4. The process as claimed in claim 1, wherein the palladiumcarbene complex comprises carbene ligands of the formula (III) or (IV),

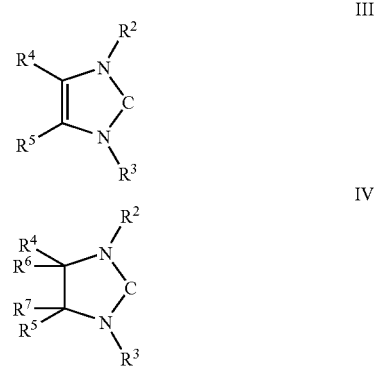

where $R^2$ and $R^3$ are each, independently of one another, a linear, branched or cyclic $C_1$–$C_{24}$-alkyl or $C_5$–$C_{18}$-aryl group and the alkyl and aryl groups optionally, independently of one another, bear the substituents —CN, —COOH, COO-alkyl-($C_1$–$C_8$), —CO-alkyl-($C_1$–$C_8$), -aryl-($C_6$–$C_{18}$), -alkyl-($C_1$–$C_{24}$), —COO-aryl-($C_6$–$C_{10}$), —CO-aryl-($C_6$–$C_{10}$), —O-alkyl-($C_1$–$C_8$), —O—CO-alkyl-($C_1$–$C_8$), —N-alkyl$_2$-($C_1$–$C_8$), —CHO, —SO$_3$H, —NH$_2$, —F, —Cl, —OH, —CF$_3$, —NO$_2$, ferrocenyl, and $R^4$ $R^7$ are each, independently of one another, hydrogen, —CN, —COOH, —COO-alkyl-($C_1$–$C_8$), —CO-alkyl-($C_1$–$C_8$), —COO-aryl-($C_6$–$C_{10}$), —CO-aryl-($C_6$–$C_{10}$), —O-alkyl-($C_1$–$C_8$), —O—CO-alkyl-($C_1$–$C_8$), —N-alkyl$_2$-($C_1$–$C_8$), —CHO, —SO$_3$H, —NH$_2$, —F, —Cl, —OH, —CF$_3$, —NO$_2$ or a linear, branched or cyclic $C_1$–$C_{24}$-alkyl or $C_6$–$C18$-aryl group and the alkyl and aryl groups, independently of one another, optionally bear the substituents —CN, —COOH, —COO-alkyl-($C_1$–$C_8$), —CO-alkyl-($C_1$–$C_8$), —-aryl-($C_6$–$C_{10}$), —COO-aryl-($C_6$–$C_{10}$), —CO-aryl-($C_6$–$C_{10}$), —O—alkyl($C_1$–$C_6$), —O—CO-alkyl-($C_1$–$C_8$), N-alkyl$_2$-($C_1$–$C_8$), —CHO, —SO$_3$H, —NH$_2$, —F, —Cl, —OH, —CF$_3$, —NO$_2$, where the radicals $R^4$ and $R^5$ optionally are part of a bridging aliphatic or aromatic ring.

5. The process as claimed in claim 1, wherein the acyclic olefin is 1,3-butadiene or isoprene.

6. The process as claimed in claim 1, wherein 1,3-butadiene is combined in admixture with other $C_4$-hydrocarbons or $C_5$-hydrocarbons.

7. The process as claimed in claim 1, wherein the nucleophile (II) or an inert organic solvent or a mixture thereof functions as a solvent.

8. The process as claimed in claim 1, wherein the reaction is conducted at temperatures ranging from 10 to 180° C. and a pressure ranging from 1 to 300 bar.

9. The process as claimed in claim 1, wherein the ratio of carbene ligand to Pd [mol/mol] ranges from 0.01:1 to 250:1.

10. The process as claimed in claim 1, wherein the palladium-carbene complex is an isolated complex.

11. The process as claimed in claim 1, wherein the palladium-carbene complex is generated in situ during the telomerization reaction.

12. The process as claimed in claim 1, wherein catalytic amounts of a basic component having a p$K_b$ of <7 are added to the reaction.

13. The process as claimed in claim 12, wherein the basic component is a compound selected from the group consisting of amines, alkali metal salts, alkaline earth metal salts and mixtures thereof.

14. The process as claimed in claim 13, wherein the basic component is present in an amount ranging from 0.01 mol % to 10 mol %, based on the olefin compound.

15. The process as claimed in claim 1, wherein the palladium concentration in the reaction mixture ranges from 0.01 to 1000 ppm.

* * * * *